(12) United States Patent
Seguin et al.

(10) Patent No.: US 6,666,883 B1
(45) Date of Patent: *Dec. 23, 2003

(54) ENDOPROSTHESIS FOR VASCULAR BIFURCATION

(76) Inventors: Jacques Seguin, 18 rue Montalivet, 75008 Paris (FR); Jean-Claude Laborde, 7 rue des Hérons, 34000 Montpellier (FR)

( * ) Notice: Subject to any disclaimer, the term of this patent is extended or adjusted under 35 U.S.C. 154(b) by 362 days.

This patent is subject to a terminal disclaimer.

(21) Appl. No.: 09/580,597

(22) Filed: May 30, 2000

Related U.S. Application Data

(63) Continuation-in-part of application No. 09/011,214, filed on Apr. 3, 1998, now Pat. No. 6,068,655.

(30) Foreign Application Priority Data

Jun. 6, 1996 (FR) ............................................. 96 07245
Jun. 5, 1997 (WO) ............................... PCT/FR97/00999

(51) Int. Cl.⁷ .................................................. A61F 2/06
(52) U.S. Cl. ..................................... 623/1.16; 623/1.15
(58) Field of Search ............................... 623/1.11–1.54

(56) References Cited

U.S. PATENT DOCUMENTS

| | | | |
|---|---|---|---|
| 4,445,896 A | 5/1984 | Gianturco |
| 4,494,531 A | 1/1985 | Gianturco |
| 4,580,568 A | 4/1986 | Gianturco |
| 4,665,906 A | 5/1987 | Jervis |
| 4,687,468 A | 8/1987 | Gianturco |
| 4,733,665 A | 3/1988 | Palmaz |
| 4,739,762 A | 4/1988 | Palmaz |
| 4,743,251 A | 5/1988 | Barra |
| 4,763,654 A | 8/1988 | Jang |
| 4,800,882 A | 1/1989 | Gianturco |
| 4,886,062 A | 12/1989 | Wiktor |
| 4,907,336 A | 3/1990 | Gianturco |
| 4,994,071 A | 2/1991 | MacGregor |
| 5,002,532 A | 3/1991 | Gaiser et al. |
| 5,035,706 A | 7/1991 | Giantureo |
| 5,041,126 A | 8/1991 | Gianturco |

(List continued on next page.)

FOREIGN PATENT DOCUMENTS

| | | |
|---|---|---|
| EP | 0 540 290 A2 | 5/1993 |
| EP | A 0 698 380 | 2/1996 |
| FR | A 2 722 678 | 1/1996 |
| FR | 2 749 500 | 12/1997 |
| JP | 62-82975 | 4/1987 |
| WO | WO-A 95 21592 | 8/1995 |
| WO | WO-A 95 32757 | 12/1995 |
| WO | WO-A 96 29955 | 10/1996 |
| WO | WO-A 97 07752 | 3/1997 |
| WO | WO 97/46174 | 12/1997 |

OTHER PUBLICATIONS

U.S. patent application Ser. No. 09/011,214, Seguin et al., filed Apr. 3, 1998.

*Primary Examiner*—Corrine McDermott
*Assistant Examiner*—Thomas Barrett
(74) *Attorney, Agent, or Firm*—Oliff & Berridge, PLC

(57) ABSTRACT

This invention features a device (1) comprising at least one radially expansible segment (7, 8) with, in the expanded state, a transversal cross section substantially greater than the transversal cross section of one of the secondary ducts (3); one segment (6) with, in the expanded state, a truncated shape, corresponding to the shape of the bifurcation at the flared transition zone (11) which separates the main duct (2) from the secondary ducts (3), and a flexible link (9) between these two segments (6, 7), enabling their adjustment relative to each other, according to the orientation of the secondary duct (3) receiving the said segment (7) relative to the flared transition zone (11).

29 Claims, 3 Drawing Sheets

U.S. PATENT DOCUMENTS

| | | |
|---|---|---|
| 5,067,957 A | 11/1991 | Jervis |
| 5,104,404 A | 4/1992 | Wolff |
| 5,135,536 A | 8/1992 | Hillstead |
| 5,176,626 A | 1/1993 | Soehendra |
| 5,190,546 A | 3/1993 | Jervis |
| 5,195,984 A | 3/1993 | Schatz |
| 5,197,978 A | 3/1993 | Hess |
| 5,219,355 A | 6/1993 | Parodi et al. |
| 5,258,000 A | 11/1993 | Gianturco |
| 5,282,824 A | 2/1994 | Gianturco |
| 5,314,444 A | 5/1994 | Gianturco |
| 5,314,472 A | 5/1994 | Fontaine |
| 5,320,602 A | 6/1994 | Karpiel |
| 5,330,482 A | 7/1994 | Gibbs et al. |
| 5,330,500 A | 7/1994 | Song |
| 5,334,208 A | 8/1994 | Soehendra et al. |
| 5,334,210 A | 8/1994 | Gianturco |
| 5,360,443 A | 11/1994 | Barone et al. |
| 5,370,683 A | 12/1994 | Fontaine |
| 5,383,892 A | 1/1995 | Cardon et al. |
| 5,387,235 A | 2/1995 | Chuter |
| D359,802 S | 6/1995 | Fontaine |
| 5,425,711 A | 6/1995 | Ressemann et al. |
| 5,441,515 A | 8/1995 | Khosravi et al. |
| 5,443,498 A | 8/1995 | Fontaine |
| 5,456,713 A | 10/1995 | Chuter |
| 5,466,242 A | 11/1995 | Mori |
| 5,507,771 A | 4/1996 | Gianturco |
| 5,514,178 A | 5/1996 | Torchio |
| 5,527,354 A | 6/1996 | Fontaine et al. |
| 5,540,701 A | 7/1996 | Sharkey et al. ............... 623/12 |
| 5,545,210 A | 8/1996 | Hess et al. |
| 5,562,697 A | 10/1996 | Christiansen |
| 5,562,724 A | 10/1996 | Vorwerk et al. |
| 5,562,726 A | 10/1996 | Chuter |
| 5,571,170 A | 11/1996 | Palmaz et al. |
| 5,571,173 A | 11/1996 | Parodi |
| 5,593,442 A | 1/1997 | Klein |
| 5,597,378 A | 1/1997 | Jervis |
| 5,603,721 A | 2/1997 | Lau et al. |
| 5,609,605 A | 3/1997 | Marshall et al. ............... 623/1 |
| 5,609,627 A | 3/1997 | Goicoechea et al. |
| 5,617,878 A | 4/1997 | Taheri |
| 5,628,788 A | 5/1997 | Pinchuk ........................ 623/12 |
| 5,632,762 A | 5/1997 | Myler |
| 5,632,763 A | 5/1997 | Glastra ............................ 623/1 |
| 5,632,771 A | 5/1997 | Boatman et al. |
| 5,632,772 A | 5/1997 | Alcime et al. ................ 623/12 |
| D380,266 S | 6/1997 | Boatman et al. |
| 5,639,278 A | 6/1997 | Dereume et al. ............. 623/12 |
| D380,831 S | 7/1997 | Kavteladze et al. |
| 5,643,277 A | 7/1997 | Soehendra et al. |
| 5,643,339 A | 7/1997 | Kavteladze et al. |
| 5,667,486 A | 9/1997 | Mikulich et al. .............. 623/1 |
| 5,683,449 A | 11/1997 | Marcade ...................... 128/898 |
| 5,690,642 A | 11/1997 | Osborne et al. |
| 5,693,084 A | 12/1997 | Chuter |
| 5,707,376 A | 1/1998 | Kavteladze et al. |
| D390,957 S | 2/1998 | Fontaine |
| 5,720,776 A | 2/1998 | Chuter et al. |
| 5,749,825 A | 5/1998 | Fischell et al. ............... 623/12 |
| 5,755,769 A | 5/1998 | Richard et al. |
| 5,755,771 A | 5/1998 | Penn et al. .................... 623/1 |
| 5,755,777 A | 5/1998 | Chuter |
| RE35,849 E | 7/1998 | Soehendra |
| 5,782,906 A | 7/1998 | Marshall et al. |
| 5,788,707 A | 8/1998 | Del Toro et al. |
| 5,800,456 A | 9/1998 | Maeda et al. |
| 5,814,061 A | 9/1998 | Osborne et al. |
| 5,824,040 A | 10/1998 | Cox et al. ...................... 623/1 |
| 5,824,042 A | 10/1998 | Lombardi et al. ............. 623/1 |
| 5,827,321 A | 10/1998 | Roubin et al. |
| 5,849,037 A | 12/1998 | Frid |
| 5,851,228 A | 12/1998 | Pinheiro ........................ 623/1 |
| 5,873,904 A | 2/1999 | Ragheb et al. |
| 5,893,887 A | 4/1999 | Jayaraman |
| 5,904,713 A | 5/1999 | Leschinsky |
| 5,922,019 A | 7/1999 | Hankh et al. |
| 5,928,280 A | 7/1999 | Hansen et al. |
| 5,938,697 A | 8/1999 | Killion et al. |
| 5,968,088 A | 10/1999 | Hansen et al. |
| 5,976,155 A | 11/1999 | Foreman et al. |
| 5,980,533 A | 11/1999 | Holman |
| 5,984,955 A | 11/1999 | Wisselink |
| 6,042,588 A | 3/2000 | Munsinger et al. |
| 6,042,606 A | 3/2000 | Frantzen |
| 6,059,813 A | 5/2000 | Vrba et al. |
| 6,063,113 A | 5/2000 | Kavteladze et al. |
| 6,086,455 A | 7/2000 | Frantzen |
| 6,093,203 A | 7/2000 | Uflacker |
| 6,096,070 A | 8/2000 | Ragheb et al. |
| 6,106,548 A | 8/2000 | Roubin et al. |
| 6,117,140 A | 9/2000 | Munsinger |
| 6,120,522 A | 9/2000 | Vrba et al. |
| 6,143,016 A | 11/2000 | Bleam et al. |
| 6,159,141 A | 12/2000 | Apple et al. |
| 6,159,238 A | 12/2000 | Killion et al. |
| 6,162,165 A | 12/2000 | Apple et al. |
| 6,183,353 B1 | 2/2001 | Frantzen |
| 6,200,336 B1 | 3/2001 | Pavcnik et al. |
| 6,210,429 B1 | 4/2001 | Vardi et al. |
| 6,221,098 B1 | 4/2001 | Wilson et al. |
| 6,228,110 B1 | 5/2001 | Munsinger |
| 6,231,598 B1 | 5/2001 | Berry et al. |
| 6,237,460 B1 | 5/2001 | Frid |
| 6,251,059 B1 | 6/2001 | Apple et al. |
| 6,254,550 B1 | 7/2001 | McNamara et al. |
| 6,261,316 B1 | 7/2001 | Shaolian et al. |
| 6,264,682 B1 | 7/2001 | Wilson et al. |
| 6,283,992 B1 | 9/2001 | Hankh et al. |
| 6,293,966 B1 | 9/2001 | Frantzen |
| 6,299,635 B1 | 10/2001 | Frantzen |
| 6,302,893 B1 | 10/2001 | Limon et al. |
| 6,302,917 B1 | 10/2001 | Dua et al. |
| 6,306,141 B1 | 10/2001 | Jervis |
| 6,325,819 B1 | 12/2001 | Pavcnik et al. |
| 6,330,884 B1 | 12/2001 | Kim |
| 6,336,938 B1 | 1/2002 | Kavteladze et al. |
| 2001/0010013 A1 | 7/2001 | Cox et al. |
| 2001/0027338 A1 | 10/2001 | Greenberg |
| 2001/0037142 A1 | 11/2001 | Stelter et al. |
| 2001/0044595 A1 | 11/2001 | Reydel et al. |

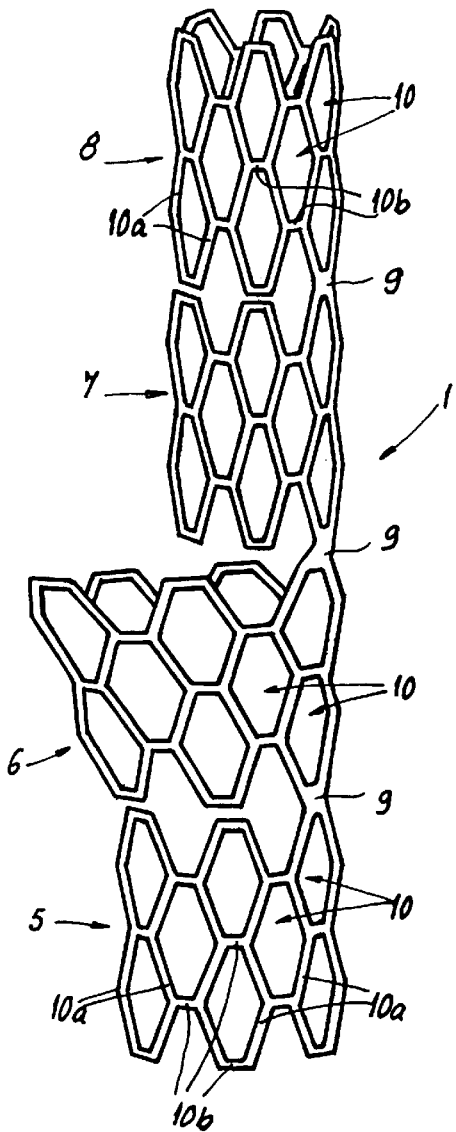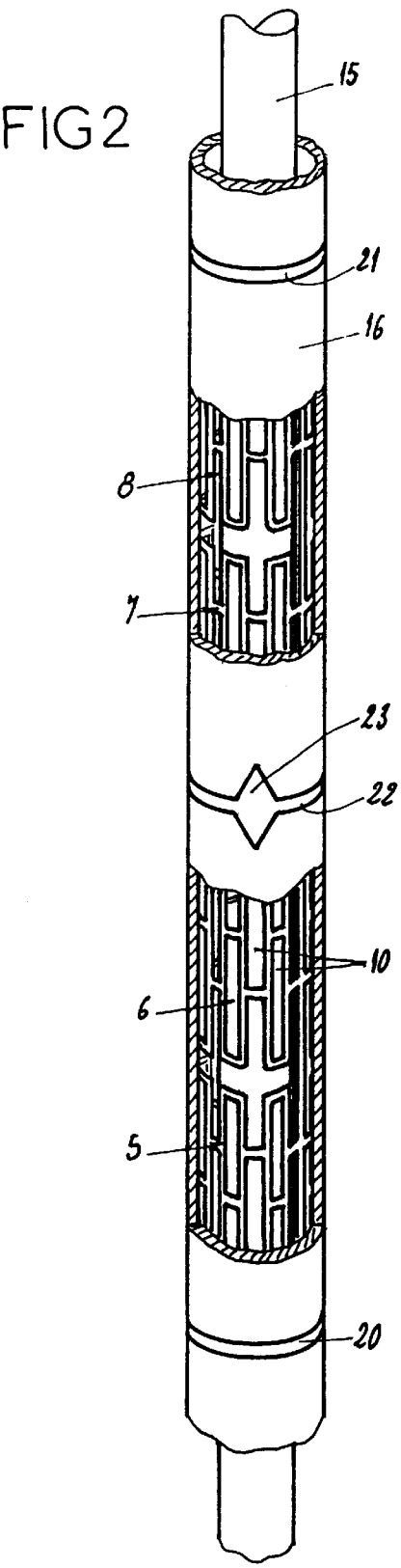

ENDOPROSTHESIS FOR VASCULAR BIFURCATION

This is a Continuation-in-Part of application Ser. No. 09/011,214 filed Apr. 3, 1998. The entire disclosure of the prior application is hereby incorporated by reference herein in its entirety. Now U.S. Pat. No. 6,068,655.

BACKGROUND OF THE INVENTION

The present invention relates to an apparatus permitting the treatment of bodily conduits in the area of a bifurcation, that is to say in the area where a principal conduit separates into two secondary conduits. It also relates to equipment for positioning this apparatus.

This apparatus can be used for the treatment of vascular bifurcations, in particular the carotid, femoral, iliac, popliteal, renal or coronary bifurcations, or nonvascular bifurcations, such as tracheal or biliary bifurcations, for example between the common bile and cystic ducts, or in the area of the bifurcation of the principal bile tract.

The treatment can consist in re-establishing the appropriate diameter of the bifurcation, in cases of arteriosclerosis or internal cell proliferation, in rectifying a localized or nonlocalized dissection in the wall of the conduit, or, in cases of aneurysm, in recreating a bifurcation of normal diameter, while eliminating the aneurysmal pouch.

DESCRIPTION OF THE PRIOR ART

It is known to treat narrowing of a rectilinear blood vessel by means of a radially expandable tubular device, commonly referred to as a stent. This device is introduced in the unexpanded state into the internal lumen of the vessel, in particular by the percutaneous route, as far as the area of narrowing. Once in place, it is expanded in such a way as to support the vessel wall and thus re-establish the appropriate cross section of the vessel.

The device can be made of a nonelastic material, and in this case is expanded by means of an inflatable balloon on which it is engaged, or can be self-expanding, that is to say made of an elastic material, expanding spontaneously when withdrawn from a sheath which is holding it in the contracted state.

U.S. Pat. Nos. 4,733,665 and 4,886,062 are illustrative of existing devices and of corresponding positioning techniques.

A conventional stent is not entirely suitable for the treatment of a narrowing situated in the area of a bifurcation, since its engagement both in the principal conduit and in one of the secondary conduits can cause immediate or delayed occlusion of the other secondary conduit.

It is known to reinforce a vascular bifurcation by means of a device comprising two elements, each formed by helical winding of a metal filament. One of the two elements has two parts of diameter corresponding respectively to the diameter of the principal vessel and to the diameter of one of the secondary vessels, and is intended to be engaged on the one hand in this principal vessel and, on the other hand, in this secondary vessel. The other element has a diameter corresponding to the diameter of the other secondary vessel and is coupled to the first element, after the latter has been put into place, by engaging one or more of its turns in the turns of the first element.

This equipment permits reinforcement of the bifurcation but appears unsuitable for treating a vascular narrowing or an occlusive lesion, in view of its structure and of the low possibility of radial expansion of its two constituent elements.

Moreover, the shape of the first element does not correspond to the shape of a bifurcation, which has a widened transitional zone between the end of the principal vessel and the ends of the secondary vessels. Thus, this equipment does not make it possible to fully support this wall or to treat a dissection in the area of this wall.

In addition, the separate positioning of these two elements seems relatively difficult.

SUMMARY OF THE INVENTION

The present invention aims to overcome these various disadvantages by making available apparatus with which it is possible to treat a pathological condition in the area of a bifurcation, by fully supporting the vascular wall and by being relatively simple to position.

The apparatus to which the invention relates comprises, in a manner known per se, segments delimiting longitudinal conduits, one of which is intended to be engaged through the bifurcation, and another of which is intended to be engaged in a secondary conduit of this bifurcation.

According to the invention, this apparatus comprises:

at least one radially expandable segment which has, in a predetermined expanded state, a cross section substantially greater than the cross section of one of the secondary conduits; and a segment which has, in a predetermined expanded state, a truncated shape, corresponding to shape of the bifurcation in the area of the widened transitional zone which separates the principal conduit from the secondary conduits.

In some embodiments of this invention, this apparatus further comprises a flexible link between these two segments.

For the sake of simplification, the segment which has, in the expanded state, a cross section substantially greater than the cross section of one of the secondary conduits will be referred to hereinafter as the "secondary segment", while the segment which has, in the expanded state, a truncated shape will be referred to hereinafter as the "truncated segment".

The secondary segment is intended to be introduced into the secondary conduit in the contracted state and to bear, in the expanded state, against the wall of this conduit. This expansion not only makes it possible to treat a narrowing or a dissection situated in the area of this conduit, but also to ensure perfect immobilization of the apparatus in the conduit.

In this position of the device, the truncated segment bears against the wall of the conduit delimiting the widened transitional zone of the bifurcation, which it is able to support fully. A narrowing or a dissection occurring at this site can thus be treated by means of this apparatus, with uniform support of the vascular wall, and thus without risk of this wall being damaged.

The two segments orient themselves suitably in relation to each other upon their expansion.

Preferably, at least the truncated segment is covered by a wall which gives it impermeability in a radial direction.

This wall makes it possible to trap, between it and the wall of the conduit, the particles which may originate from the lesion being treated, such as arteriosclerotic particles or cellular agglomerates, and thus to avoid the migration of these particles in the body.

Moreover, the apparatus can permit treatment of an aneurysm by guiding the liquid through the bifurcation and thereby preventing stressing of the wall forming the aneurysm.

The segments can be made from tubes of material of a different diameter, with the tube for the truncated segment having a larger diameter than the tube for the secondary segment. The tubes may be comprised of the same material. The use of tubes of different diameters results in the truncated segment having a larger radial force, especially at larger diameters.

The apparatus can comprise several secondary segments, placed one after the other, to ensure supplementary support of the wall of the secondary conduit and, if need be, to increase the anchoring force of the device in the bifurcation. To this same end, the apparatus can comprise, on that side of the truncated segment directed toward the principal conduit, at least one radially expandable segment having, in the expanded state, a cross section which is substantially greater than the cross section of the principal conduit.

These various supplementary segments may or may not be connected to each other and to the two aforementioned segments by means of flexible links, such as those indicated above.

The flexible links can be integral with one of the segments and separately connected to the other segment, or the flexible links can be separate pieces of material separately connected to both segments, such as by welding.

Preferably, the flexible link between two consecutive segments is made up of one or more bridges of material connecting the two adjacent ends of these two segments. Said bridge or bridges are advantageously made of the same material as that forming the segments.

According to a preferred embodiment of the invention, each segment has a meshwork structure, the meshes being elongated in the longitudinal direction of the device, and each one having a substantially hexagonal shape; the meshes of the truncated segment have a width which increases progressively in the longitudinal sense of the device, in the direction of the end of this segment having the greatest cross section in the expanded state.

This increase in the width of the meshes is the result of an increase in the length of the edges of the meshes disposed longitudinally and/or an increase in the angle formed between two facing edges of the same mesh.

In addition, the truncated segment can have an axis not coincident with the longitudinal axis of the secondary segment, but oblique in relation to this axis, in order to be adapted optimally to the anatomy of the bifurcation which is to be treated. In this case, the widths of the meshes of the truncated segment also increase progressively, in the transverse sense of the device, in the direction of a generatrix diametrically opposite that located in the continuation of the bridge connecting this segment to the adjacent segment.

The apparatus can be made of a metal with shape memory, which becomes malleable, without elasticity, at a temperature markedly lower than that of the human body, in order to permit retraction of the apparatus upon itself, and to allow it to recover its neutral shape at a temperature substantially corresponding to that of the human body. This metal is preferably the nickel/titanium alloy known by the name NITINOL.

The equipment for positioning the apparatus comprises, in a manner known per se, means for permitting the expansion of this apparatus when the latter is in place. These means can comprise a removable sheath in which the device is placed in the contracted state, when this device is made of an elastic material, or a support core comprising an inflatable balloon on which the device is placed, when this device is made of a nonelastic material.

In either case, this equipment comprises, according to the invention, means with which it is possible to identify, through the body of the patient, the longitudinal location of the truncated segment, so that the latter can be correctly positioned in the area of the widened zone of the bifurcation.

In the case where the expansion of this same segment is not uniform in relation to the axis of the device, the equipment additionally comprises means with which it is possible to identify, through the body of the patient, the angular orientation of the device in relation to the bifurcation, so that that part of this segment having the greatest expansion can be placed in a suitable manner in relation to the bifurcation.

BRIEF DESCRIPTION OF THE DRAWINGS

To ensure that it is fully understood, the invention is again described hereinbelow with reference to the attached diagrammatic drawing which shows, by way of nonlimitiing example, two preferred embodiments of the device to which the invention relates.

FIG. 1 is a side view thereof, according to a first embodiment;

FIG. 2 is a perspective view of this device in a state of radial contraction, and, in partial cutaway, of the equipment allowing it to be positioned;

DESCRIPTION OF THE PREFERRED EMBODIMENTS

Figure 3:
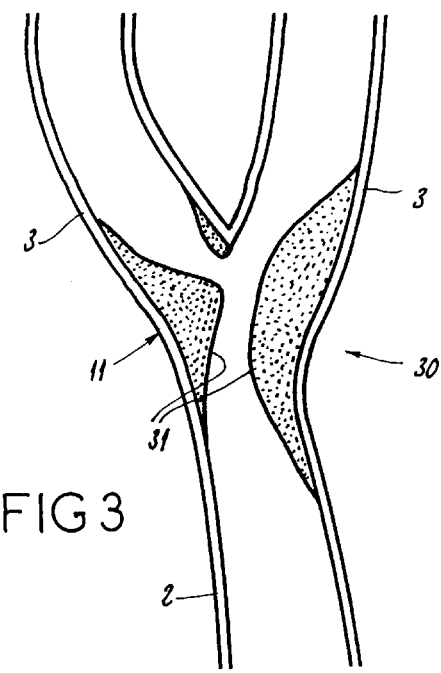
FIG. 3 is a longitudinal sectional view of the bifurcation to be treated.

FIG. 1 shows an expandable device 1 permitting the treatment of bodily conduits in the area of a bifurcation, that is to say, as is shown in FIG. 3, in the area where a principal conduit 2 separates into two secondary conduits 3.

The device 1 comprises four successive segments 5, 6, 7, 8, of meshwork structure, which are connected to one another via three bridges of material 9.

The meshes 10 of these segments are elongated in the longitudinal direction of the device 1 and have in each case a substantially hexagonal shape.

The segment 5 has a tubular shape and has a diameter which is substantially greater than the diameter of the principal conduit 2.

The segment 6 has meshes 10 whose width increases progressively, compared to that of the meshes of the segment 5, on the one hand in the longitudinal sense of the device 1, in the direction of the end of the segment 6 situated opposite the segment 5, and, on the other hand, in the transverse sense of the device 1, in the direction of a generatrix diametrically opposite that located in the continuation of the bridge 9.

This increase in the width of the meshes 10 results from an increase in the length of the edges 10a of the meshes 10 disposed longitudinally, as well as an increase in the angle formed between two facing edges 10a.

This segment 6 thus has a truncated shape with an axis which is oblique in relation to the longitudinal axis of the device 1. This shape corresponds to the shape of the bifurcation in the area of the widened transitional zone 11 which separates the end of the principal conduit 2 from the ends of the secondary conduits 3.

The segments 7 and 8 are identical to each other and have a tubular shape with a diameter which is substantially greater than the diameter of one of the secondary conduits 3.

The bridges of material 9 connect the adjacent ends of the segments 5 to 8 and have a small width, so that they can undergo a certain flexion, making it possible to orient these segments in relation to one another, in particular the segment 6 in relation to the segment 7.

The device 1 is made by appropriate cutting of a sheet of nickel/titanium alloy known by the name NITINOL, then folding the resulting blank into a circle and welding the parts of this blank which come into proximity with each other.

This alloy is malleable at a temperature of the order of 10° C. but can recover its neutral shape at a temperature substantially corresponding to that of the human body.

FIG. 2 shows the device 1 in a state of radial contraction, obtained by cooling its constituent material. During this contraction, the edges 10a pivot in relation to the transverse edges 10b of the meshes 10, in such a way that the meshes 10 have, in this sate of contraction, a substantially rectangular shape.

By virtue of this contraction, the segments 5 to 8 have a cross section which is smaller than that of the conduits 2 and 3, and they can be introduced into these, as will be described hereinafter.

The device 1 is engaged on a central support core 15, and is then contracted radially on the latter. This core 15 comprises an axial abutment such as a shoulder (not visible in FIG. 2) which has a diameter smaller than that of the device 1 when this device is expanded, but greater than the diameter of this device 1 when the latter is contracted. This abutment consequently permits the axial immobilization of the device 1 on the core 15 when the latter is contracted.

A sheath 16 is then engaged on the device 1 in order to hold it in its contracted state. This sheath 16 includes four radiopaque markers 20, 21, 22, 23 impressed on it, containing, for example, a barium compound. Three markers 20, 21, 22 have an annular 5 shape and extend round the whole periphery of the sheath 16. They are situated, respectively, in the area of the free ends of the segments 5 and 8 and in the area of the bridge 9 separating the segments 6 and 7. The fourth marker 23 is situated at substantially the halfway point of the generatrix of the segment 6 situated in the continuation of the bridge 9 and of the diametrically opposite generatrix. It has a diamond shape and a small thickness.

Figure 4:
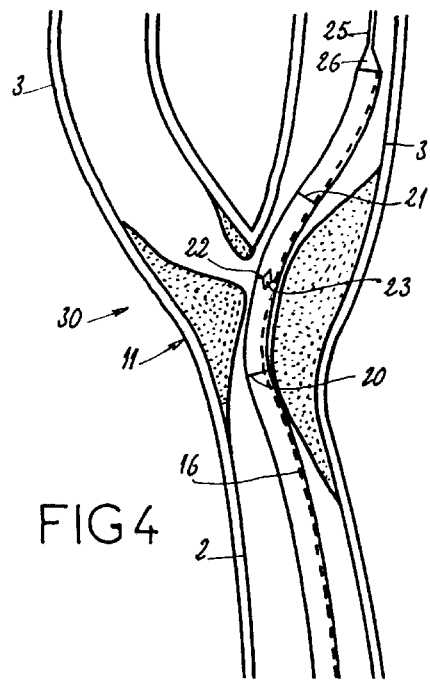
FIGS. 4 to 6 are views of this bifurcation similar to FIG. 3, during three successive stages of positioning of the device.
Figure 5:
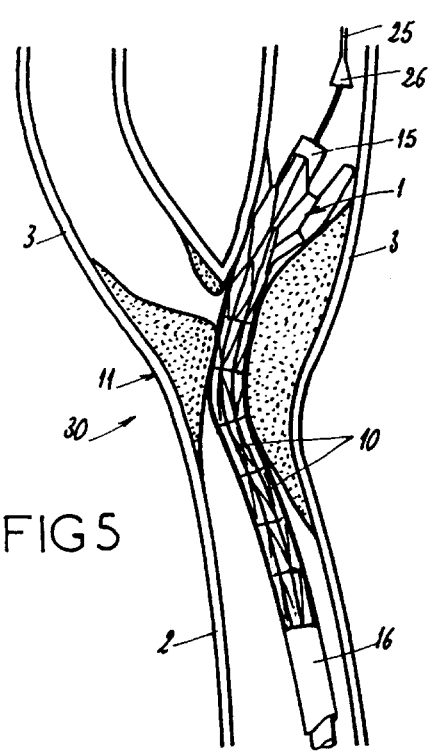
Figure 6:
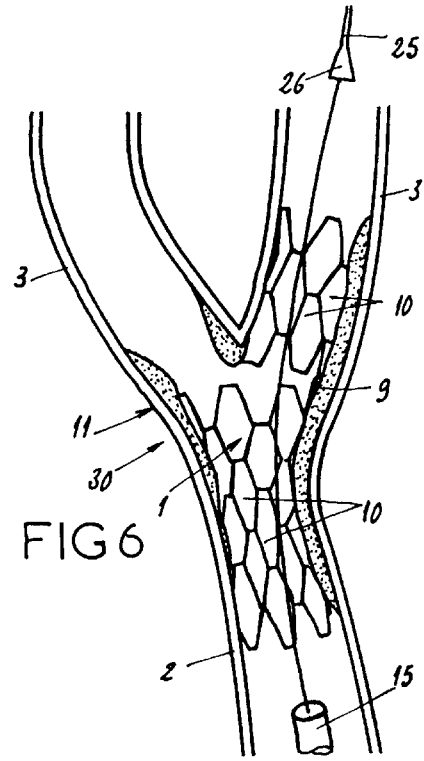

The core 15 has a longitudinal axial hole permitting its engagement on a guide wire 25 (FIGS. 4 to 6). This wire 25 can be engaged, by the percutaneous route, in the conduit 2, by way of the zone 11, and then in one of the conduits 3, through which it can slide, and comprises a cone 26 of synthetic material, situated in front of the assembly consisting of core 15, device 1 and sheath 16.

The bifurcation 30 shown in FIG. 3 has excrescences 31 which create a narrowing in cross section, which impedes the flow of the liquid circulating in the conduits 2 and 3. In the case of a vascular bifurcation, these excrescences are due, for example, to arteriosclerosis or cellular growth.

The device 1 permits treatment of this bifurcation by re-establishing the appropriate diameter of the conduits 2, 3 and of the widened zone 11.

In practice, as can be seen in FIG. 4, the assembly consisting of core 15, device 1 and sheath 16 is engaged on the wire 25 as far as the cone 26. By means of its sliding action, this wire 25 permits the engagement and then the guiding of this assembly in the conduit 2, the zone 11 and then the conduit 3. The cone 26 facilitates the sliding of the assembly and reduces the risk of trauma.

The marker 22 makes it possible to visualize, with the aid of a suitable radiography apparatus, the position of the bridge 9 separating the segments 6 and 57, and thus to visualize the location of the segment 6 so that the latter can be correctly positioned in relation to the widened zone 11.

With the markers 20 and 21 it is possible to ensure that the segments 5 and 8 are correctly positioned, respectively, in the principal conduit 2 and the secondary conduit 3.

The marker 23 is, for its part, visible in a plan view or an edge view, depending on whether it is oriented perpendicular or parallel to the radius of the radiography apparatus. It thus makes it possible to identify the angular orientation of the device 1 in relation to the bifurcation 30, so that the part of the segment 6 having the greatest expansion can be placed in an appropriate manner in relation to the zone 11.

The sheath 16, which has a length such that it opens out beyond the opening having permitted introduction of the assembly, is then progressively withdrawn, as is shown in FIGS. 5 and 6, in order to permit the complete expansion of the device 1.

The latter is reheated by the body temperature, and this permits its expansion. After complete expansion of the device 1, the core 15 and the wire 25 are withdrawn.

Figure 7:
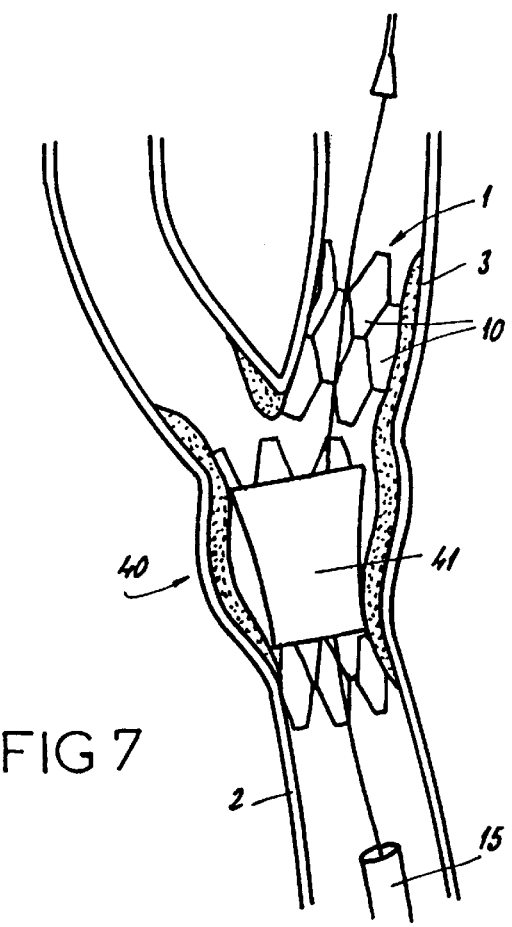
FIG. 7 is a view, similar to FIG. 3, of a bifurcation presenting an aneurysm, in which the device is placed.

FIG. 7 shows that the device 1 can also be used to treat an aneurysm 40. The segment 6 and a part of the segment 5 are then covered by a polyester film 41, impermeable to the liquid circulating in the conduits 2 and 3, which film is sewn onto them. The device then guides this liquid through the bifurcation 30 and consequently prevents stressing of the wall forming the aneurysm 40.

Figure 8:
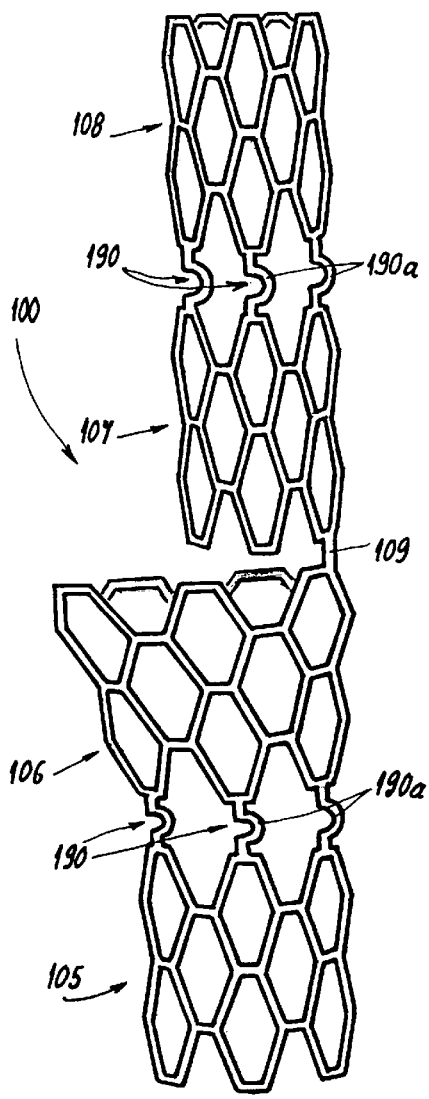
FIG. 8 is a side view of the device according to a second embodiment.

FIG. 8 shows a device 100 according to the invention, having segments 105, 106, 107, 108 and a bridge 109 connecting the segments 106 and 107, with a structure similar to that of the segments 5 to 8 and of the bridge 9 in the device shown in FIG. 1.

In the device 100, two consecutive segments, excluding the segments 106 and 107, are connected by six. omega-shaped bridges 190. The curved central part 190a of these bridges 190 has a multidirectional elasticity permitting the appropriate longitudinal orientation of the various segments in relation to one another.

The advantage of these bridges 190 is that they provide the device with longitudinal continuity, which facilitates the passage of said device into a highly curved zone and which eliminates the need to reduce this curvature, which is always dangerous in the cases of arteriosclerosis, so as to permit the passage of the device.

The invention thus provides a device permitting the treatment of a pathological condition in the area of a bifurcation 30. This device has the many advantages indicated above, in particular those of ensuring a perfect support of the vessel wall and of being relatively simple to position.

It goes without saying that the invention is not limited to the embodiment described hereinabove by way of example, but instead embraces all the variant embodiments.

Thus, the device 1, 100 can comprise several segments 5, 8, 105, 108 placed one after the other, in order to ensure supplementary support and, if need be, to increase the hold of the device in the bifurcation 30.

The core 15 could comprise an inflatable balloon, either to effect the expansion of the device 1, in the case where the latter is made of a nonelastic material, or to ensure the total expansion of a self-expanding device 1 after the latter has been put into place.

The markers 20 to 23 could be impressed on the core 15 or directly on the device 1, in particular on the bridge 9, 109, and not on the sheath 16.

The segment 6, 106 could have an axis coincident with the longitudinal axis of the device, and not oblique in relation to this axis, if such is rendered necessary by the anatomy of the bifurcation which is to be treated.

In addition, the segment 7, 107 could itself have, in the expanded state, a widened shape corresponding to the shape of the widened connecting zone via which, in certain bifurcations, the secondary conduits 3 are connected to the widened transition zone 11. This segment 7, 107 would thus have a shape corresponding to the shape of this widened connecting zone, and would ensure perfect support thereof.

The bridges 190 between two consecutive segments could be greater or smaller in number than six, and they could have a shape other than an omega shape, permitting their multi-directional elasticity, and in particular a V shape or W shape.

In addition, in other embodiments, the bridges 9 and 190 could be integral with one of the connected segments and separately connected, such as by welding, to the other connected segment. For example, bridge 9 which connects segments 6 and 7 could be integral with segment 6 and connected to segment 7, or integral with segment 7 and connected to segment 6.

In yet other embodiments, bridges 9 and 190 could be separate pieces of materials which are separately connected to segments 5, 6, 7 and 8 (or segments 105, 106, 107 and 108), such as by welding. In all of these embodiments, the segments 5 and 6 (and 105 and 106) can be made from different tubes of material than segments 7 and 8 (and 107 and 108). The tube from which segments 5 and 6 (and 105 and 106) are made may be a smaller diameter than the tube from which segments 5 and 6 (and 105 and 106) are made. The respective tubes may or may not be made of the same material.

Accordingly, bridges 9 and 190 can be made from one of these tubes, and thus be integral with segments 5 and 6 or segments 7 and 8 (or segments 105 and 106 or segments 107 and 108) or bridges 9 and 190 can be separate pieces of material.

When segments 5 and 6 (and 105 and 106) are made from tubes of a smaller diameter than segments 7 and 8 (and 107 and 108), the radial force of segments 7 and 8 (and 107 and 108) is larger than the radial force of segments 5 and 6 (and 105 and 106), especially at larger cross sections.

In further embodiments, bridges 9 and 190 are omitted such that the individual segments are spaced apart as necessary during installation and use. These individual segments are still delivered and implanted in the same core and sheath assembly.

What is claimed is:

1. A device for treatment of bodily conduits in an area of a bifurcation where a principal conduit separates into two secondary conduits, the device comprising non-overlapping segments delimiting longitudinal conduits, one of said segments being configured to be engaged in the primary conduit in the area of bifurcation, and another of said segments being configured to be engaged in a secondary conduit of the bifurcation;

at least one radially expandable first said segment having, in a predetermined expanded state, a cross section substantially greater than a cross section of one of the secondary conduits;

at least one radially expandable second said segment having a first end and a second end, said first end being capable of expanding to a greater diameter than said second end, and having in a predetermined expanded state, a truncated shape, conforming to a shape of the bifurcation in the area of a widened transitional zone that separates the principal conduit from the secondary conduits; and a flexible link extending between and being separately connected to at least one of said first segment and said first end of said second segment, permitting said segments to be oriented in relation to one another on the basis of the orientation of the secondary conduit, which receives said first segment, in relation to said widened transitional zone, wherein said second segment has an axis not coincident with a longitudinal axis of said first segment, but oblique in relation to the axis of said first segment, in order to be adapted optimally to the anatomy of the bifurcation which is to be treated;

wherein the cross section of said first segment in the predetermined expanded state is less than the cross section of the first and second ends of said second segment when the second segment is in its predetermined expanded state.

2. The device as claimed in claim 1, wherein said first and second segments are made from first and second tubes of material, respectively, and the second tube has a larger diameter than the first tube.

3. The device as claimed in claim 2, wherein said flexible link is welded to said first and second segments.

4. The device as claimed in claim 2, wherein said tubes are comprised of the same material.

5. The device as claimed in claim 4, wherein the at least one bridge of material is made of the same material as the material forming said first and second segments.

6. The device as claimed in claim 1, wherein said first segment comprises several radially expandable segments placed one after the other and having, in the predetermined expanded state, a cross section that is substantially greater than the cross section of one of the secondary conduits.

7. The device as claimed in claim 1, wherein the flexible link between said first and second segments is made up of at least one bridge of material connecting adjacent ends of said first and second segments.

8. The device as claimed in claim 1, wherein each of said first and second segments has a meshwork structure formed of meshes elongated in a longitudinal direction of the device, each mesh having a substantially hexagonal shape, wherein the meshes of said second segment have a width which increases progressively in the longitudinal direction of the device with the meshes toward the end of said second segment having the greatest cross section in the expanded state.

9. A device for treatment of bodily conduits in an area of bifurcation where a principal conduit separates into two secondary conduits, the device having non-overlapping segments delimiting longitudinal conduits, one of said segments being configured to be engaged in the primary conduit in the area of bifurcation, and another of said segments being configured to be engaged in a secondary conduit of the bifurcation, said device comprising:

at least one radially expandable first segment, which has, in a predetermined expanded state, a substantially cylindrical shape and a cross section substantially greater than a cross section of one of the secondary conduits;

at least one radially expandable second segment, which has a first end and a second end, said first end being capable of expanding to a greater diameter than said second end, and which has, in a predetermined expanded state, a truncated substantially conical shape in which said first end conforms to a shape of the bifurcation in the area of a widened transitional zone that separates the principal conduit from the secondary conduits when said first segment is in a said secondary conduit; and flexible link extending between and being connected to at least one of said first segment and said first end of said second segment;

wherein the cross section of said first segment in the predetermined expanded state is less than the cross section of the first and second ends of said second segment when the second segment is in its predetermined expanded state.

10. A device according to claim 9, wherein said first and second segments are made from first and second tubes of material, respectively, and the second tube has a larger diameter than the first tube.

11. A device according to claim 10, wherein said flexible link is welded to said first and second segments.

12. A device according to claim 11, wherein the flexible link permits said first and second segments to be oriented in relation to one another on the basis of the orientation of said secondary conduit, which receives said first segment, in relation to said widened transitional zone.

13. A device according to claim 12, wherein the second segment has an axis not coincident with the longitudinal axis of said first segment but oblique in relation to the axis of said first segment, in order to be adapted optimally to the anatomy of the bifurcation which is to be treated.

14. A method of treating bodily conduits in an area of bifurcation where a principal conduit separates into two secondary conduits, said method comprising:

supporting at least one of the two secondary conduits with at least one radially expandable first segment, which has, in a predetermined expanded state, a substantially cylindrical shape and a cross section substantially greater than a cross section of said one of the secondary conduits;

supporting the principal conduit with at least one radially expandable second segment having a first end and a second end, said first end being capable of expanding to a greater diameter than said second end, and which has, in a predetermined expanded state, a truncated substantially conical shape which conforms to a shape of the bifurcation in the area of a widened transitional zone that separates the principal conduit from the secondary conduits, wherein the first end of the second segment is linked to said first segment by a flexible link which is separately connected to at least one of the first and second segments and the first segment and the second segment do not overlap; and locating said second segment so that it adapts to the shape of the widened transitional zone of the bifurcation upon expansion;

wherein the cross section of the first segment in the predetermine expanded state is less than the cross section of the first and second ends of said second segment when the second segment is in its predetermined expanded state.

15. The method of claim 14, wherein said first and second segments are made from first and second tubes of material, respectively, and the second tube has a larger diameter than the first tube.

16. The method of claim 15, wherein said flexible link is welded to said first and second segments.

17. The method of claim 14, wherein said second segment has an axis not coincident with a longitudinal axis of said first segment, but oblique in relation to the axis of said first segment, in order to be adapted optimally to the anatomy of the bifurcation which is to be treated.

18. The method of claim 14, further comprising:

positioning said first and second segments respectively in said one of the secondary conduits and in the principal conduit at the same time, using a support core and a sheath which prevents said first and second segments from expanding prior to being properly positioned respectively in the one of the secondary conduits and the principal conduit, and then withdrawing said support core and sheath.

19. The method of claim 14, further comprising:

positioning said first and second segments respectively in said one of the secondary conduits and in the principal conduit prior to allowing said first and second segments to expand.

20. The method of claim 14, wherein said first segment comprises several radially expandable segments placed one after the other and having, in the expanded state, a substantially cylindrical shape and a cross section that is substantially greater than the cross section of said one of the secondary conduits.

21. The method of claim 14, further comprising:

positioning, on a side of said second segment directed toward the principal conduit, at least one radially expandable third segment having, in an expanded state, a substantially cylindrical shape and a cross section that is substantially greater than the cross section of the principal conduit.

22. A method of treating body conduits in an area of bifurcation where a principal conduit separates into multiple secondary conduits, the principal conduit increasing in cross section to the junction with the multiple secondary conduits, said method comprising:

supporting at least one of the secondary conduits with at least one radially expanded first segment of an apparatus for treatment of body conduits, which said first segment has, in a predetermined fully expanded state, a substantially cylindrical shape and a cross section greater than a cross section of said one of the secondary conduits; and supporting the principal conduit with at least one radially expanded second segment of the apparatus for treatment of body conduits, which said second segment has, in a predetermined fully expanded state, a truncated substantially conical shape which conforms to the shape of the increasing cross section of the principal conduit;

wherein the first segment and the second segment do not overlap.

23. The method according to claim 22, wherein the cross section of said first segment in the predetermined expanded state is less than the cross section of the first and second ends of said second segment when the second segment is in its predetermined expanded state.

24. The method according to claim 22, further comprising the step of:

forming the first and segments from first and second tubes of material, respectively, wherein the second tube has a larger diameter than the first tube.

25. The method according to claim 24, wherein the tubes are comprised of the same material.

26. The method according to claim 22, said first and second segments being free of any link for connecting said first and second segments.

27. A method of treating bodily conduits in an area of bifurcation where a principal conduit separates into at least two secondary conduits, said method comprising:

locating at least one radially expandable device having a first end and a second end, said first end being capable of expanding to a greater diameter than said second end and said device having, in a predetermined expanded state, a truncated substantially conical shape that conforms to and supports an increasing cross section of the principal conduit in the area of a widened transitional zone that separates the principal conduit from the secondary conduits, in said principal conduit so that it adapts to the shape of the widened transitional zone of the bifurcation upon expansion, and does not overlap any other stent body.

28. A method of treating bodily conduits in an area of bifurcation where a principal conduit separates into at least two secondary conduits and where the principal conduit increases in cross section to the junction with the secondary conduits, comprising:

supporting the principal conduit with at least one radially expandable device having (1) a first end and a second end, and (2) in a predetermined filly expanded state, a substantially truncated conical shape such that the first end has a greater diameter than the second end and the first end conforms to and supports the increasing cross section of the principal conduit at the area of bifurcation, said device being located in said principal conduit with said first end opening out in the direction of said secondary conduits and said device not overlapping any other stent body.

29. A method of treating bodily conduits in an area of bifurcation where a principal conduit separates into at least two secondary conduits, the principal conduit increasing in cross section to the junction with the secondary conduits, comprising:

supporting the principal conduit with at least one radially expandable device having a first end and a second end, said first end being capable of expanding to a greater diameter than said second end, and which has, in a predetermined expanded state, a truncated substantially conical shape that conforms to the increasing cross section of the principal conduit; and locating said device so that the first end opens towards the secondary conduits upon expansion of the device and does not overlap any other stent body.

* * * * *